(12) United States Patent
Norman et al.

(10) Patent No.: US 8,809,594 B2
(45) Date of Patent: Aug. 19, 2014

(54) DUAL CATALYST SYSTEM FOR THE SELF-CONDENSATION OF ALCOHOLS

(71) Applicant: Eastman Chemical Company, Kingsport, TN (US)

(72) Inventors: David William Norman, Kingsport, TN (US); Damon Ray Billodeaux, Longview, TX (US); Melissa Dawn Page, Gate City, VA (US)

(73) Assignee: Eastman Chemical Company, Kingsport, TN (US)

( * ) Notice: Subject to any disclaimer, the term of this patent is extended or adjusted under 35 U.S.C. 154(b) by 1 day.

(21) Appl. No.: 13/624,035

(22) Filed: Sep. 21, 2012

(65) Prior Publication Data

US 2014/0088326 A1 Mar. 27, 2014

(51) Int. Cl.
*C07C 45/45* (2006.01)
*C07C 29/141* (2006.01)

(52) U.S. Cl.
USPC ............ 568/461; 568/465; 568/880; 568/881; 568/885; 568/905

(58) Field of Classification Search
CPC ........ C07C 45/72; C07C 47/02; C07C 45/73; C07C 47/21; C07C 29/34; C07C 31/125; C07C 29/38
USPC .................. 568/461, 465, 880, 881, 905, 840
See application file for complete search history.

(56) References Cited

U.S. PATENT DOCUMENTS

| | | | |
|---|---|---|---|
| 4,101,586 A | 7/1978 | Deem et al. | |
| 4,316,990 A | 2/1982 | Morris | |
| 5,777,183 A | 7/1998 | Mueller et al. | |
| 6,419,797 B1 | 7/2002 | Scherf et al. | |
| 7,501,546 B2 | 3/2009 | Koivusalmi et al. | |
| 7,663,006 B2 | 2/2010 | Oota et al. | |
| 7,700,810 B2 | 4/2010 | Kourtakis et al. | |
| 7,700,811 B2 | 4/2010 | Kourtakis et al. | |
| 7,977,517 B2 | 7/2011 | Cortright et al. | |
| 8,048,290 B2 | 11/2011 | Knuuttila et al. | |
| 8,080,695 B2 | 12/2011 | Tsuchida et al. | |
| 8,143,469 B2 | 3/2012 | Koivusalmi et al. | |
| 8,187,347 B2 | 5/2012 | Sakuma et al. | |
| 2010/0286455 A1 | 11/2010 | Ozer et al. | |
| 2010/0298614 A1 | 11/2010 | Ozer et al. | |
| 2011/0021845 A1 | 1/2011 | Zim et al. | |
| 2011/0245554 A1 | 10/2011 | Huber et al. | |
| 2012/0144733 A1 | 6/2012 | Truitt | |
| 2012/0157732 A1 | 6/2012 | Truitt | |

FOREIGN PATENT DOCUMENTS

| | | |
|---|---|---|
| CN | 101659597 | 3/2010 |
| DE | 10232458 | 7/2003 |
| EP | 0440420 | 7/1991 |
| JP | 61059612 B | 3/1982 |

OTHER PUBLICATIONS

Carlini et al. Selective Synthesis of 2-ethyl-1-hexanol from *n*-butanol Through the Guerbet Reaction by Using Bifunctional Catalysts Based on Copper or Palladium Precursors and Sodium Butoxide, J. Mol. Cat. [Online], 2004, vol. 212, pp. 65-70.

Carlini et al. Selective Synthesis of Isobutanol by Means of the Guerbet Reaction Part 2. Reaction of Methanol/ethanol and Methanol/ethanol/*n*-propanol Mixtures Over Copper based/MeONa Catalytic Systems, J. Mol. Cat. [Online], 2003, vol. 200, pp. 137-146.

Carlini et al. Synthesis of Isobutanol by the Guerbet Condensation of Methanol with *n*-propanol in the Presence of Heterogeneous and Homogeneous Palladium-based Catalytic Systems, J. Mol. Cat. [Online], 2003, vol. 204-205, pp. 721-728.

Guerbet, M. Comptes Rendu Acad. Sci., 1899, vol. 128, p. 1002.

Ndou, A. S. et al. Dimerisation of Ethanol to Butanol over Solid-base Catalysts, Applied Cat. A, 2003, vol. 251, p. 337.

Reddy, B. M. et al. A Single-step Synthesis of Isobutyraldehyde from Methanol and Ethanol over CuO—ZnO—Al$_2$O$_3$, J. Chem. Soc., Chem. Commun., 1992, pp. 997-998.

Reddy, B. M. et al. Vapour Phase Synthesis of Isobutyraldehyde from Methanol and Ethanol over Mixed Oxide Supported Vanadium Oxide Catalysts, Res. Chem. Intermed., 1997, vol. 23, No. 8, pp. 703-713.

Shen, W. et al. Vapor Phase Butanal Self-condensation over Unsupported and Supported Alkaline Earth Metal Oxides, J. Catal., 2012, vol. 286, pp. 703-713.

Veibel, S. et al. On the Mechanism of the Guerbet Reaction, Tetrahedron, 1967, vol. 23, p. 1723.

Carlini, Carlo et al.; "Guerbet condensation of methanol with *n*-propanol to isobutyl alcohol over heterogeneous copper chromite/Mg—Al mixed oxides catalysts"; Journal of Molecular Catalysis A: Chemical, 220; 2004; pp. 215-220.

*Primary Examiner* — Sikarl Witherspoon
(74) *Attorney, Agent, or Firm* — Jennifer R. Knight

(57) ABSTRACT

Disclosed is a process for the production of higher aldehydes from lower alcohols using a two-stage vapor phase heterogeneous catalyst system. Ethanol feeds afford aldehydes such as butyraldehyde and crotonaldehyde while butanol feeds yield 2-ethylhexanal and 2-ethylhexenal. Higher product selectivities are obtained when the alcohol is first dehydrogenated in the upper catalyst stage followed by aldol condensation of the resulting lower aldehyde to a higher aldehyde.

27 Claims, 1 Drawing Sheet

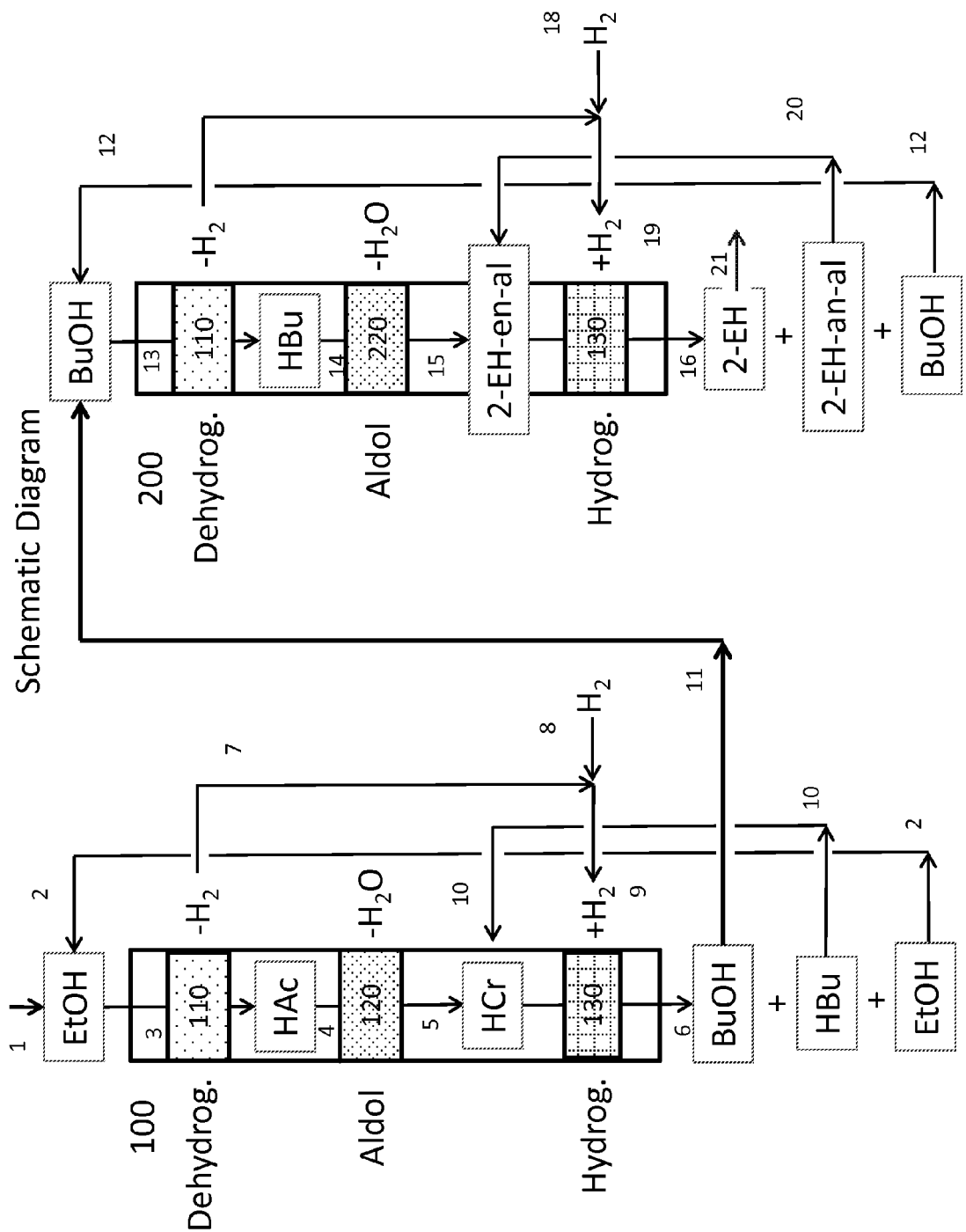

US 8,809,594 B2

DUAL CATALYST SYSTEM FOR THE SELF-CONDENSATION OF ALCOHOLS

FIELD OF THE INVENTION

This invention relates to a vapor phase, two-stage process for making higher-molecular-weight aldehydes and/or alcohols from lower-molecular-weight alcohols. Specifically the invention relates to a process for producing butanol from ethanol and/or 2-ethylhexanol from butanol.

BACKGROUND OF THE INVENTION

The conversion of alcohols to higher molecular weight compounds—particularly industrially relevant alcohols—has been the subject of various investigations for many years. The self-condensation of an alcohol to an alcohol with double the molecular weight was first reported by Marcel Guerbet nearly 100 years ago. The formation of "Guerbet alcohols" requires very high concentrations of a strongly basic alkoxide metal salt. Separation of the alcohol product from the catalyst and potential recovery and recycle or disposal of the catalyst can be expensive and environmentally challenging. In addition, the coproduction of water can rapidly deactivate the catalyst if the water is not efficiently removed during the reaction. Solubility problems associated with the alkoxide metal salt can also lead to processing concerns.

Typically, higher-molecular-weight alcohols, such as 2-ethylhexanol (2-EH or 2-EH-ol), are produced by the aldol condensation of aldehydes, for example normal-butyraldehyde (n-butyraldehyde). The aldol condensation reaction utilizes a homogeneous sodium or potassium hydroxide catalyst. The thus produced unsaturated aldehyde is further reduced over a nickel catalyst in the presence of hydrogen to produce the saturated alcohol. Disadvantages of this process include coproduction of salts and the dependence on petroleum products needed for the generation of the aldehyde starting material through hydroformylation, the so-called OXO process.

Recent focus on the production of biologically based alcohols has thrust the production of commercially relevant chemicals from these "green" raw materials into the forefront. Of particular interest is the use of ethanol from fermentation of corn, sugar cane, and other plant materials. Butanol produced from fermentation by genetically engineered microorganisms, referred to as "bio-butanol", is also of growing interest. Conversion of bio-based ethanol and butanol to butyraldehyde, 2-ethylhexanol, 2-ethylhexenal or 2-ethylhexanal are of particular interest.

A vapor phase process utilizing a heterogeneous catalyst would preclude the product/catalyst separation issues in classical Guerbet chemistry and the conventional 2-EH process. Other attempts at heterogeneous catalysts have focused on a single catalyst capable of carrying out Guerbet condensations. These catalysts have been plagued by either low conversion and/or low selectivity to the desired products. However, by utilizing a dual heterogeneous catalyst system in a vapor phase reactor, one can efficiently produce the Guerbet alcohol, the unsaturated aldehyde, or the saturated aldehyde with higher selectivity. Subsequent hydrogenation over a polishing bed can give the desired products—reduced alcohol or saturated aldehyde.

DESCRIPTION OF THE DRAWINGS

FIG. 1 is a schematic of an embodiment of the present invention for producing 2-ethylhexanol from ethanol.

SUMMARY OF THE INVENTION

We have discovered a process for the preparation of a higher-molecular-weight alcohol comprising
  (A) feeding a lower-molecular-weight alcohol to a first reactor zone comprising a heterogeneous dehydrogenation catalyst to produce a lower-molecular-weight aldehyde containing stream;
  (B) feeding the lower-molecular-weight aldehyde containing stream to a second reactor zone comprising a heterogeneous aldol condensation catalyst to produce a higher-molecular-weight aldehyde containing stream; and
  (C) feeding the higher-molecular-weight aldehyde containing stream and hydrogen to a third reactor zone comprising a heterogeneous hydrogenation catalyst to produce an effluent comprising a higher-molecular-weight alcohol;
wherein the process is conducted in the vapor phase.

The present invention provides in a second embodiment a process for the preparation of 2-EH compounds comprising
  (A) feeding n-butanol to a reactor zone comprising a heterogeneous dehydrogenation catalyst and a heterogeneous aldol condensation catalyst; and
  (B) producing a reactor effluent comprising at least one compound selected from the group consisting of 2-ethylhexanal (2-EH-anal) and 2-ethylhexenal (2-EH-enal);
wherein the process is conducted in the vapor phase.

The present invention provides in a third embodiment a process for the preparation of 2-ethylhexanol comprising
  (A) feeding n-butanol to a first reactor zone comprising a heterogeneous dehydrogenation catalyst to produce a butyraldehyde containing stream;
  (B) feeding the butyraldehyde containing stream to a second reactor zone comprising a heterogeneous aldol condensation catalyst to produce a 2-ethylhexanal and/or 2-ethylhexenal containing stream; and
  (C) hydrogenating the 2-ethylhexanal and/or 2-ethylhexenal containing stream to form a crude product comprising 2-ethylhexanal and/or 2-ethylhexanol;
wherein the process is conducted in the vapor phase.

DETAILED DESCRIPTION

The present invention provides in a first embodiment a process for the preparation of a higher-molecular-weight alcohol comprising
  (A) feeding a lower-molecular-weight alcohol to a first reactor zone comprising a heterogeneous dehydrogenation catalyst to produce a lower-molecular-weight aldehyde containing stream;
  (B) feeding the lower-molecular-weight aldehyde containing stream to a second reactor zone comprising a heterogeneous aldol condensation catalyst to produce a higher-molecular-weight aldehyde containing stream; and
  (C) feeding the higher-molecular-weight aldehyde containing stream and hydrogen to a third reactor zone comprising a heterogeneous hydrogenation catalyst to produce an effluent comprising a higher-molecular-weight alcohol;
wherein the process is conducted in the vapor phase.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

It is to be understood that the mention of one or more process steps does not preclude the presence of additional process steps before or after the combined recited steps or intervening process steps between those steps expressly identified. Moreover, the lettering of process steps or ingredients is a convenient means for identifying discrete activities or ingredients and the recited lettering can be arranged in any sequence, unless otherwise indicated.

As used herein the term "and/or", when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The term "lower-molecular-weight alcohol", as used herein, refers to a reactant intended to produce an alcohol product wherein the alcohol product has a higher molecular weight (almost double) than the "lower-molecular-weight alcohol". The term, "higher-molecular-weight alcohol", as used herein refers to the product of a reaction involving an alcohol reactant wherein the alcohol reactant has a lower molecular weight than the "higher-molecular-weight alcohol".

The term "lower-molecular-weight aldehyde", as used herein, refers to a reactant intended to produce an aldehyde product wherein the aldehyde product has a higher molecular weight (almost double) than the "lower-molecular-weight aldehyde". The term "higher-molecular-weight aldehyde", as used herein, refers to the product of a reaction involving an aldehyde reactant wherein the aldehyde reactant has a lower molecular weight than the "higher-molecular-weight aldehyde". For example, lower-molecular-weight alcohol, ethanol, can be dehydrogenated to produce lower-molecular-weight aldehyde, acetaldehyde, which can undergo an aldol condensation to produce higher-molecular-weight aldehyde, crotonaldehyde, which can be hydrogenated to produce higher-molecular-weight alcohol, butanol.

The term "heterogeneous dehydrogenation catalyst", as used herein, refers to a solid catalyst useful in the conversion of an alcohol to an aldehyde.

The term "heterogeneous aldol condensation catalyst", as used herein, refers to a solid catalyst useful in the aldol condensation of a lower-molecular-weight aldehyde to a higher-molecular-weight aldehyde.

The term "heterogeneous hydrogenation catalyst", as used herein, refers to a solid catalyst useful in the conversion of an unsaturated or saturated aldehyde to a saturated aldehyde and/or alcohol.

The term "catalyst bed", as used herein, refers to the physical grouping of the solid catalyst particles.

The term "reactor zone", as used herein, refers to the part of the process wherein an alcohol and/or an aldehyde are fed, a heterogeneous catalyst is fed to or contained therein, and dehydrogenation, aldol condensation, and/or hydrogenation occurs.

The term "vapor phase", as used herein, refers to reactor conditions wherein the feed alcohol and ensuing products are above their dew point. Dew point is defined as the temperature below which liquid condensation takes place for a gaseous mixture having a condensable material at a given pressure.

The term "2-EH compounds", or "2-EH oxygenated products" as used herein, refers to 2-ethylhexanol, 2-ethylhexanal and 2-ethylhexenal. When the oxygenated products have four carbons, "oxygenated products", as used herein, refers to crotonaldehyde, butyraldehyde, and butanol The terms "co-mingled", "co-mixed" or "dry mixed" as used herein, refer to a physical mixture of two or more distinct heterogeneous solid catalysts.

The term "anatase", as used herein, refers to a crystal phase of titania ($TiO_2$) that occurs naturally. Anatase is a distorted octahedral phase of titania as opposed to the symmetric octahedral rutile phase. The term "modified anatase", as used herein, refers to anatase modified or functionalized with vanadia ($V_2O_5$) groups.

The term "effluent", as used herein refers to the stream exiting a reactor zone.

The term "single-pass yield", as used herein refers to the number of moles of higher molecular weight alcohol and/or higher molecular weight aldehyde present in the reactor effluent divided by the number of moles of lower molecular weight alcohol consumed times 2. For example the single-pass yield of lower-molecular-weight alcohol to higher-molecular-weight alcohol equals conversion of lower-molecular-weight alcohol times selectivity to higher-molecular-weight alcohol, or 2*(moles of higher-molecular-weight alcohol in effluent)/(moles of lower-molecular-weight alcohol fed).

The lower-molecular-weight alcohol fed to the first reactor zone comprising a heterogeneous dehydrogenation catalyst can be any primary alcohol comprising 1 to 8 carbon atoms, 1 to 6 carbon atoms, 1 to 5 carbon atoms, 1 to 4 carbon atoms, 2 to 8 carbon atoms, 2 to 6 carbon atoms, 2 to 5 carbon atoms, or 2 to 4 carbon atoms. The lower-molecular-weight alcohol can be selected from the group consisting of methanol, ethanol, n-propanol, n-butanol, and i-butanol. The lower-molecular-weight alcohol can be selected from the group consisting of ethanol, n-propanol, n-butanol, and i-butanol. The lower-molecular-weight alcohol can be ethanol and/or n-butanol. The lower-molecular-weight alcohol can be n-butanol. The lower-molecular-weight aldehyde in the lower-molecular-weight aldehyde containing stream is produced by dehydrogenating the lower-molecular-weight alcohol. The lower-molecular-weight aldehyde can be any aldehyde comprising 1 to 8 carbon atoms, 1 to 6 carbon atoms, 1 to 5 carbon atoms, 1 to 4 carbon atoms, 2 to 8 carbon atoms, 2 to 6 carbon atoms, 2 to 5 carbon atoms, or 2 to 4 carbon atoms. The lower-molecular-weight aldehyde can be selected from the group consisting of formaldehyde, acetaldehyde, propionaldehyde, butyraldehyde, and iso-butyraldehyde (2-butanal). The lower-molecular-weight aldehyde can be selected from the group consisting of acetaldehyde, propionaldehyde, butyraldehyde, and isobutyraldehyde (2-butanal). The lower-molecular-weight aldehyde can be acetaldehyde. The lower-molecular-weight aldehyde can be n-butyraldehyde.

The higher-molecular-weight aldehyde in the higher-molecular-weight aldehyde containing stream can be produced by an aldol condensation reaction of the lower-molecular-weight aldehyde. The higher-molecular-weight aldehyde can be any aldehyde comprising an even number of carbon atoms in the range 2 to 16 carbon atoms, 2 to 12 carbon atoms, 2 to 10 carbon atoms, 2 to 8 carbon atoms, 4 to 16 carbon atoms, 4 to 12 carbon atoms, 4 to 10 carbon atoms 4 to 8 carbon atoms. The higher-molecular-weight aldehyde can be selected from the group consisting of n-butyraldehyde, crotonaldehyde, 2-ethylbutanal, 2-ethylhexanal and/or 2-ethylhexenal, 4-ethylhexanal and/or 4-ethyl-2-hexenal, 2,4-diethylhexanal and/or 2,4-diethyl-2-hexenal, 2,4-diethyloctanal, 2,4-diethyl-2-octenal, 2,4,6-triethyldecanal, 2,4,6,8-tetraethyldodecanal. The higher-molecular-weight aldehyde can be butyraldehyde and/or crotonaldehyde. The higher-molecular-weight aldehyde can be 2-ethylhexanal and/or 2-ethylhexenal.

The higher-molecular-weight alcohol can be produced by hydrogenating the higher-molecular-weight aldehyde in the higher-molecular-weight aldehyde containing stream. The higher-molecular-weight alcohol can be any alcohol comprising an even number of carbon atoms in the range of 2 to 16 carbon atoms, 2 to 12 carbon atoms, 2 to 10 carbon atoms, 2 to 8 carbon atoms, 4 to 16 carbon atoms, 4 to 12 carbon atoms, 4 to 10 carbon atoms 4 to 8 carbon atoms. The higher-molecular-weight alcohol can be at least one selected from the group consisting of n-butanol, 2-ethylhexanol, 2-ethylbutanol, 4-ethylhexanol, 2,4-diethylhexanol, 2,4-diethyloctanol, 2,4,6-triethyldecanol, and 2,4,6,8-tetraethyldodecanol. The higher-molecular-weight alcohol can be n-butanol and/or 2-ethylhexanol. The higher-molecular-weight alcohol can be 2-ethylhexanol.

The non-oxidative dehydrogenation catalyst can be chosen from any known dehydrogenation catalysts. Particularly useful dehydrogenation catalysts include supported copper oxides such as copper chromites, copper zinc oxides and copper oxide on alumina, silica or titania. These catalysts typically dehydrogenate the alcohol substrate via an endothermic process which liberates the respective aldehyde and a molar equivalent of hydrogen. Oxidative dehydrogenation catalysts such as supported silver or gold materials may also be used in this invention. These catalysts operate via an exothermic process that liberates the respective aldehyde and a molar equivalent of water.

A first reactor zone comprises a heterogeneous dehydrogenation catalyst such that the catalyst is used for the dehydrogenation reaction in any of the normal means known to those skilled in the art. For example, the catalyst can be contained in the reactor zone such that the feed flows through the catalyst particles. Alternatively the catalyst can be fed to the first reactor zone, exit the first reactor zone, be separated from the lower-molecular-weight aldehyde containing stream by means known to those skilled in the art, and recycled back to the first reactor zone.

The second catalyst in the dual catalyst system is an aldol condensation catalyst chosen from those known to effectively carry out the aldol condensation of aldehydes. The aldol condensation reaction can be catalyzed by acid, base and acid-base bifunctional catalysts including alkaline earth metal oxides such as magnesium oxide or calcium oxide, alkali promoted alkaline earth metal oxides such as lithium, sodium, potassium or cesium promoted magnesium oxide, supported alkali catalysts, acidic zeolites, alkali modified zeolites, magnesium-aluminum hydrotalcites, anionic clay, zirconia, sulfate modified zirconia, lanthanum oxide, niobium oxide, cerium oxide, titanium oxide. Particularly useful is anatase titania since it is known to be an effective aldol condensation catalyst. For this reason, unmodified anatase titania and titania promoted with vanadium are particularly useful in the application of this invention.

The vanadium modified anatase catalyst is typically promoted with a given weight percent of $V_2O_5$ based on the total weight of the $V_2O_5$ modified anatase. The amount of $V_2O_5$ in the $V_2O_5$ modified anatase ranges from 1 weight percent to 30 weight percent, 1 weight percent to 20 weight percent, 1 weight percent to 15 weight percent, 1 weight percent to 10 weight percent, 1 weight percent to 5 weight percent, 2 weight percent to 20 weight percent, 2 weight percent to 15 weight percent, 2 weight percent to 10 weight percent, 2 weight percent to 5 weight percent, 5 weight percent to 20 weight percent, 5 weight percent to 15 weight percent, or 5 weight percent to 10 weight percent.

The surface area of the vanadium modified anatase catalysts can range from 10 $m^2/g$ to 150 $m^2/g$, 10 $m^2/g$ to 100 $m^2/g$, 10 $m^2/g$ to 50 $m^2/g$, 20 $m^2/g$ to 150 $m^2/g$, 20 $m^2/g$ to 100 $m^2/g$, 20 $m^2/g$ to 50 $m^2/g$, 30 $m^2/g$ to 150 $m^2/g$, 30 $m^2/g$ to 100 $m^2/g$, 30 $m^2/g$ to 50 $m^2/g$.

Unmodified anatase can be purchased directly from commercial suppliers. Modified anatase is prepared by methods known to those skilled in the art such as incipient wetness, sol-gel methods and surface impregnation. Typically, unmodified anatase is modified by one of these methods using precursors such as vanadium oxides, ammonium metavanadate, vanadyl oxalate or vanadium chloride.

A second reactor zone comprises a heterogeneous aldol condensation catalyst such that the catalyst is used for the aldol condensation reaction in any of the normal means known to those skilled in the art. For example, the catalyst can be contained in the reactor zone such that the feed flows through the catalyst particles. Alternatively the catalyst can be fed to the second reactor zone, exit the second reactor zone, be separated from the higher-molecular-weight aldehyde containing stream by means known to those skilled in the art, and recycled back to the second reactor zone.

The heterogeneous hydrogenation catalyst is not particularly limited, and can be any heterogeneous hydrogenation catalyst known to those skilled in the art. For example, supported and unsupported nickel catalysts, such as Rainey Ni, are ideal for converting aldehydes such as 2-ethylhexenal, 2-ethylhexanal, crotonaldehyde or butyraldehyde to alcohols such as 2-ethylhexanol or butanol. The nickel may be supported on any known support such as, but not limited to, carbon, alumina, silica, zirconia, titania, clays, zeolites, or other supports. The nickel may be promoted or unpromoted with other metals such as Pd, Pt, Mo, W, or Cr. Supported ruthenium or copper catalysts may also be used for this application. Palladium catalysts supported on carbon, alumina, silica, zirconia, titania, clays, zeolites, or other supports may be used to reduce unsaturated aldehydes such as 2-ethylhexenal or crotonaldehyde to saturated aldehydes such as 2-ethylhexanal or butyraldehyde.

A third reactor zone comprises a heterogeneous hydrogenation catalyst such that the catalyst is used for the hydrogenation reaction as is known to those skilled in the art. For example, the catalyst can be contained in the reactor zone such that the feed flows through the catalyst particles. Alternatively the catalyst can be fed to the third reactor zone, exit the third reactor zone, be separated from the effluent comprising the higher-molecular-weight alcohol by means known to those skilled in the art, and recycled back to the third reactor zone.

The three reactor zones may be physically distinct, either within one piece of equipment, or in separate pieces of equipment. In one aspect, the reactions are carried out in three distinct zones with three distinct catalyst beds. In another aspect, the first reactor zone and the second reactor zone are combined such that the dehydrogenation catalyst and the aldol condensation catalyst are co-mingled. The reactor zones can be oriented vertically or horizontally. For vertically oriented reactor zones, the vapor feed may enter at the bottom and move up the reactor or may enter at the top and move down the reactor. The type of reactor is not particularly limiting. Suitable reactor's include but are not limited to fixed bed reactors, fluidized bed reactors, tubular reactors, stirred tank reactors, Berty reactors, and the like.

The process conditions are not particularly limited so long as materials remain in the vapor phase. The temperature of the three reactor zones can be the same or different. The temperature can range from 100° C. to 500° C., 100° C. to 350° C., 100° C. to 300° C., or 100° C. to 250° C. The pressure of the three reactor zones can be the same or different. The pressure can range from 0 psig to 1000 psig, 0 psig to 500 psig, 0 psig to 300 psig, 0 psig to 250 psig, 0 psig to 200 psig, 0 psig to 150 psig, 0 psig to 100 psig, or 0 psig to 50 psig.

The feeding of the lower-molecular-weight alcohol to the first reactor zone can occur in conjunction with feeding of a diluent gas. The diluent gas can comprise nitrogen, argon, oxygen, air, hydrogen, helium, or mixtures thereof. The molar ratio of the diluent gas to the lower-molecular-weight alcohol can range from 0.01:1 to 20:1, 0.01:1 to 10:1, 0.01:1 to 5:1, 0.1:1 to 20:1, 0.1:1 to 10:1, or 0.1:1 to 5:1.

In one aspect of the first embodiment the temperature ranges from 100° C. to 500° C., the pressure ranges from 0 psig to 250 psig; and the process further comprises feeding a diluent gas selected from at least one of the group consisting of nitrogen, argon, oxygen, air, hydrogen, and helium to the first reactor zone.

In the process of the present embodiment, the single-pass yield of lower-molecular-weight alcohol to higher-molecular-weight alcohol ranges from 1 percent to 80 percent, 1 percent to 60 percent, 1 percent to 40 percent, 1 percent to 25 percent, 5 percent to 80 percent, 5 percent to 60 percent, 5 percent to 40 percent, 5 percent to 25 percent, 10 percent to 80 percent, 10 percent to 60 percent, 10 percent to 40 percent, or 10 percent to 25 percent.

The present invention provides in a second embodiment a process for the preparation of 2-EH compounds comprising
(A) feeding n-butanol to a first reactor zone comprising a heterogeneous dehydrogenation catalyst and a heterogeneous aldol condensation catalyst; and
(B) producing a reactor effluent comprising at least one compound selected from the group consisting of 2-ethylhexanal (2-EH-anal) and 2-ethylhexenal (2-EH-enal); wherein the process is conducted in the vapor phase.

The non-oxidative dehydrogenation catalyst can be chosen from any known dehydrogenation catalysts. Particularly useful dehydrogenation catalysts include supported copper oxides such as copper chromites, copper zinc oxides and copper oxide on alumina, silica or titania. These catalysts typically dehydrogenate the alcohol substrate via an endothermic process which liberates the respective aldehyde and a molar equivalent of hydrogen. Oxidative dehydrogenation catalysts such as supported silver or gold materials may also be used in this invention. These catalysts operate via an exothermic process that liberates the respective aldehyde and a molar equivalent of water.

The second catalyst in the dual catalyst system is an aldol condensation catalyst chosen from those known to effectively carry out the aldol condensation of aldehydes. The aldol condensation reaction can be catalyzed by acid, base and acid-base bifunctional catalysts including alkaline earth metal oxides such as magnesium oxide or calcium oxide, alkali promoted alkaline earth metal oxides such as lithium, sodium, potassium or cesium promoted magnesium oxide, supported alkali catalysts, acidic zeolites, alkali modified zeolites, magnesium-aluminum hydrotalcites, anionic clay, zirconia, sulfate modified zirconia, lanthanum oxide, niobium oxide, cerium oxide, titanium oxide. Particularly useful is anatase titania since it is known to be an effective aldol condensation catalyst. For this reason, unmodified anatase titania and titania promoted with vanadium are particularly useful in the application of this invention.

The vanadium modified anatase catalyst is typically promoted with a given weight percent of $V_2O_5$ based on the total weight of the $V_2O_5$ modified anatase. The amount of $V_2O_5$ in the $V_2O_5$ modified anatase ranges from 1 weight percent to 30 weight percent, 1 weight percent to 20 weight percent, 1 weight percent to 15 weight percent, 1 weight percent to 10 weight percent, 1 weight percent to 5 weight percent, 2 weight percent to 20 weight percent, 2 weight percent to 15 weight percent, 2 weight percent to 10 weight percent, 2 weight percent to 5 weight percent, 5 weight percent to 20 weight percent, 5 weight percent to 15 weight percent, or 5 weight percent to 10 weight percent.

The surface area of the vanadium modified anatase catalysts can range from 10 $m^2/g$ to 150 $m^2/g$, 10 $m^2/g$ to 100 $m^2/g$, 10 $m^2/g$ to 50 $m^2/g$, 20 $m^2/g$ to 150 $m^2/g$, 20 $m^2/g$ to 100 $m^2/g$, 20 $m^2/g$ to 50 $m^2/g$, 30 $m^2/g$ to 150 $m^2/g$, 30 $m^2/g$ to 100 $m^2/g$, 30 $m^2/g$ to 50 $m^2/g$.

Unmodified anatase can be purchased directly from commercial suppliers. Modified anatase is prepared by methods known to those skilled in the art such as incipient wetness, sol-gel methods, and surface impregnation. Typically, unmodified anatase is modified by one of these methods using precursors such as vanadium oxides, ammonium metavanadate, vanadyl oxalate or vanadium chloride.

In the present embodiment, the first reactor zone comprises a heterogeneous dehydrogenation catalyst and a heterogeneous aldol condensation catalyst. In one aspect, the heterogeneous dehydrogenation catalyst and the heterogeneous aldol condensation catalyst are co-mingled in a catalyst bed. In another aspect, the heterogeneous dehydrogenation catalyst is in a first catalyst bed and the heterogeneous aldol condensation catalyst is in a second catalyst bed. The first catalyst bed and the second catalyst bed may be in the same or different pieces of process equipment. Either or both catalysts may be contained in the first reactor zone, or exit the first reactor zone be separated from reactants and/or products and recycled back to the first reactor zone.

A second reactor zone comprises a heterogeneous hydrogenation catalyst such that the catalyst is used for the hydrogenation reaction as is known to those skilled in the art. For example, the catalyst can be contained in the reactor zone such that the feed flows through the catalyst particles. Alternatively the catalyst can be fed to the second reactor zone, exit the second reactor zone, be separated from the effluent comprising the higher-molecular-weight alcohol by means known to those skilled in the art, and recycled back to the second reactor zone.

The reactor zones can be oriented vertically or horizontally. For vertically oriented reactor zones, the vapor feed may enter at the bottom and move up the reactor or may enter at the top and move down the reactor. The type of reactor is not particularly limiting. Suitable reactor's include but are not limited to fixed bed reactors, fluidized bed reactors, tubular reactors, stirred tank reactors, Berty reactors and the like.

The process conditions are not particularly limited so long as materials remain in the vapor phase. The temperature can range from 100° C. to 500° C., 100° C. to 350° C., 100° C. to 300° C., or 100° C. to 250° C. The pressure can range from 0 psig to 1000 psig, 0 psig to 500 psig, 0 psig to 300 psig, 0 psig to 250 psig, 0 psig to 200 psig, 0 psig to 150 psig, 0 psig to 100 psig, or 0 psig to 50 psig.

The feeding of the n-butanol to the reactor zone can be accompanied with feeding of a diluent gas. The diluent gas can comprise nitrogen, argon, oxygen, air, hydrogen, helium and mixtures thereof. The molar ratio of the diluent gas to the n-butanol can range from 0.01:1 to 20:1, 0.01:1 to 10:1, 0.01:1 to 5:1, 0.1:1 to 20:1, 0.1:1 to 10:1, or 0.1:1 to 5:1.

In one aspect of the second embodiment the temperature ranges from 100° C. to 500° C., the pressure ranges from 0 psig to 250 psig; and the process further comprises feeding a diluent gas selected from at least one of the group consisting of nitrogen, argon, oxygen, air, hydrogen, and helium to the reactor zone.

Another aspect of the second embodiment further comprises (C) feeding the reactor effluent to a second reactor zone comprising a heterogeneous hydrogenation catalyst to produce a crude product comprising 2-ethylhexanal and/or 2-ethylhexanol. The heterogeneous hydrogenation catalyst is not particularly limited and can be any heterogeneous hydrogenation catalyst known to one skilled in the art. Some non-limiting examples of heterogeneous hydrogenation catalyst are supported and unsupported nickel catalysts, such as Rainey Ni, are ideal for converting aldehydes such as 2-ethylhexenal and 2-ethylhexanal, to alcohols such as 2-ethylhexanol. The nickel may be supported on any known support such as, but not limited to, carbon, alumina, silica, zirconia, titania, clays, zeolites, or other supports. The nickel may be promoted or unpromoted with other metals such as Pd, Pt, Mo, W, or Cr. Supported ruthenium or copper catalysts may also be used for this application. Palladium catalysts supported on carbon, alumina, silica, zirconia, titania, clays, zeolites, or other supports may be used to reduce unsaturated aldehydes such as 2-ethylhexenal to saturated aldehydes such as 2-ethylhexanal.

In the process of the present embodiment, the single-pass yield of n-butanol to at least one compound selected from the group consisting of 2-ethylhexanal and 2-ethylhexenal ranges from 1 percent to 80 percent, 1 percent to 60 percent, 1 percent to 40 percent, 1 percent to 25 percent, 5 percent to 80 percent, 5 percent to 60 percent, 5 percent to 40 percent, 5 percent to 25 percent, 10 percent to 80 percent, 10 percent to 60 percent, 10 percent to 40 percent, or 10 percent to 25 percent.

In the process of the present embodiment, the single-pass yield of n-butanol to the sum of 2-ethylhexanal and 2-ethylhexenal ranges from 1 percent to 80 percent, 1 percent to 60 percent, 1 percent to 40 percent, 1 percent to 25 percent, 5 percent to 80 percent, 5 percent to 60 percent, 5 percent to 40 percent, 5 percent to 25 percent, 10 percent to 80 percent, 10 percent to 60 percent, 10 percent to 40 percent, or 10 percent to 25 percent.

The present invention provides in a third embodiment a process for the preparation of 2-ethylhexanol comprising (A) feeding n-butanol to a first reactor zone comprising a heterogeneous dehydrogenation catalyst to produce a butyraldehyde containing stream;
(B) feeding the butyraldehyde containing stream to a second reactor zone comprising a heterogeneous aldol condensation catalyst to produce a 2-ethylhexanal and/or 2-ethylhexenal containing stream; and
(C) hydrogenating the 2-ethylhexanal and/or 2-ethylhexenal containing stream to form a crude product comprising 2-ethylhexanal and/or 2-ethylhexanol;
wherein the process is conducted in the vapor phase.

The description of the catalysts, vapor phase, temperature, pressure, diluent gas, hydrogenation, and single pass yield of the second embodiment apply to third embodiment. The description of the reactor zones for the first embodiment to imply to this embodiment.

For example, the heterogeneous aldol condensation catalyst can comprise $V_2O_5$ modified anatase. The heterogeneous aldol condensation catalyst can comprise $V_2O_5$ wherein the amount of $V_2O_5$ ranges from 1 weight percent to 30 weight percent based upon the total weight of the catalyst. The surface area of the $V_2O_5$ modified anatase can range from 10 $m^2/g$ to 150 $m^2/g$. The process conditions can include temperature ranges from 100° C. to 500° C. and pressure ranges from 0 psig to 250 psig, or temperature ranges from 100° C. to 350° C. and pressure ranges from 0 psig to 100 psig. In another aspect, the process further comprises feeding a diluent gas selected from at least one of the group consisting of nitrogen, argon, oxygen, air, hydrogen, and helium to the first reactor zone. The molar ratio of the diluent gas to n-butanol ranges from 0.1:1 to 20:1. The single-pass yield of n-butanol to 2-ethylhexanal and/or 2-ethylhexanol can range from 5 percent to 60 percent.

FIG. 1 presents a non-limiting embodiment of the instant invention described herein in detail. In the invention as laid out in the schematic diagram of FIG. 1, ethanol 1 is combined with ethanol recycle 2 to produce ethanol feed 3 which is fed to Reactor 100. Reactor 100 contains dehydrogenation catalyst bed 110, aldol condensation catalyst bed 120, and hydrogenation catalyst bed 130. The ethanol feed 3 passes through dehydrogenation catalyst bed 110 and is converted to acetaldehyde containing stream 4. Acetaldehyde containing stream 4 passes through aldol condensation catalyst bed 120 where it is converted to crotonaldehyde containing stream 5. Crotonaldehyde containing stream 5 passes through hydrogenation catalyst bed 130 where it exits Reactor 100 as effluent 6 comprising butanol 11, butyraldehyde 10, and unreacted ethanol recycle 2. These components can be separated with 6 butyraldehyde 10 recycled to the dehydrogenation step, and ethanol recycle 2 recycled to the top of Reactor 100. In FIG. 1, butanol 11 is combined with butanol recycle 12 to produce the butanol feed 13 which is fed to Reactor 200. Reactor 200 contains dehydrogenation catalyst bed 210, aldol condensation catalyst bed 220, and hydrogenation catalyst bed 230. Butanol feed 13 passes through dehydrogenation catalyst bed 210 and is converted to butyraldehyde containing stream 14. Butyraldehyde containing stream 14 passes through aldol condensation catalyst bed 220 where it is converted to 2-ethylhexanal containing stream 15. 2-ethylhexanal containing stream 15 passes through hydrogenation catalyst bed 230 where it exits Reactor 200 as effluent 16 comprising 2-ethylhexanol 21, 2-ethylhexanal 20, and unreacted butanol recycle 12. These components can be separated with 2-ethylhexanal 20 recycled to the dehydrogenation step, and butanol recycle 12 recycled to the top of Reactor 200.

Listing of Non-Limiting Embodiments

Embodiment A is a process for the preparation of a higher-molecular-weight alcohol comprising
(A) feeding a lower-molecular-weight alcohol to a first reactor zone comprising a heterogeneous dehydrogenation catalyst to produce a lower-molecular-weight aldehyde containing stream;
(B) feeding the lower-molecular-weight aldehyde containing stream to a second reactor zone comprising a heterogeneous aldol condensation catalyst to produce a higher-molecular-weight aldehyde containing stream; and
(C) feeding the higher-molecular-weight aldehyde containing stream and hydrogen to a third reactor zone comprising a heterogeneous hydrogenation catalyst to produce an effluent comprising a higher-molecular-weight alcohol;
wherein the process is conducted in the vapor phase.

The process of Embodiment A wherein the heterogeneous aldol condensation catalyst comprises $V_2O_5$ modified anatase.

The process of Embodiment A or Embodiment A with one or more of the intervening features wherein the lower-molecular-weight alcohol is selected from the group consisting of methanol, ethanol, n-propanol, n-butanol, and i-butanol.

The process of Embodiment A or Embodiment A with one or more of the intervening features wherein the temperature ranges from 100° C. to 500° C., or from 100° C. to 350° C., the pressure ranges from 0 psig to 250 psig or from 0 psig to 100 psig; and further comprising feeding a diluent gas selected from at least one of the group consisting of nitrogen, argon, oxygen, air, hydrogen, and helium to the first reactor zone.

The process of Embodiment A or Embodiment A with one or more of the intervening features wherein the single-pass yield of lower-molecular-weight alcohol to higher-molecular-weight alcohol ranges from 1 percent to 80 percent, from 5 percent to 60 percent, or from 10 percent to 40 percent.

Embodiment B is a process for the preparation of 2-EH compounds comprising
(A) feeding n-butanol to a reactor zone comprising a heterogeneous dehydrogenation catalyst and a heterogeneous aldol condensation catalyst; and
(B) producing a reactor effluent comprising at least one compound selected from the group consisting of 2-ethylhexanal (2-EH-anal) and 2-ethylhexenal (2-EH-enal);
wherein the process is conducted in the vapor phase.

The process of Embodiment B wherein the heterogeneous dehydrogenation catalyst and the heterogeneous aldol condensation catalyst are commingled in a catalyst bed or alternatively Embodiment B wherein the heterogeneous dehydrogenation catalyst is in a first catalyst bed and the heterogeneous aldol condensation catalyst is in a second catalyst bed.

The process of Embodiment B or Embodiment B with one or more of the intervening features further comprising (C) feeding the reactor effluent to a second reactor zone comprising a heterogeneous hydrogenation catalyst to produce a crude product comprising of 2-ethylhexanal and/or 2-ethylhexanol.

The process of Embodiment B or Embodiment B with one or more of the intervening features wherein the heterogeneous aldol condensation catalyst comprises $V_2O_5$ modified anatase.

The process of Embodiment B or Embodiment B with one or more of the intervening features wherein the heterogeneous aldol condensation catalyst comprises $V_2O_5$ modified anatase and wherein the amount of $V_2O_5$ ranges from 1 weight percent to 30 weight percent, from 2 weight percent to 20 weight percent, or from 5 weight percent to 15 weight percent based upon the total weight of the $V_2O_5$ modified anatase.

The process of Embodiment B or Embodiment B with one or more of the intervening features wherein the temperature ranges from 100° C. to 500° C., or from 100° C. to 350° C.

The process of Embodiment B or Embodiment B with one or more of the intervening features wherein the pressure ranges from 0 psig to 250 psig, or from 0 psig to 100 psig.

The process of Embodiment B or Embodiment B with one or more of the intervening features further comprising feeding a diluent gas selected from at least one of the group consisting of nitrogen, argon, oxygen, air, hydrogen, and helium to the first reactor zone.

The process of Embodiment B or Embodiment B with one or more of the intervening features wherein the single-pass yield of the n-butanol to the 2-ethylhexanal and/or the 2-ethylhexenal ranges from 1 percent to 80 percent, from 10 percent to 60 percent, or from 10 percent to 40 percent.

The process of Embodiment B or Embodiment B with one or more of the intervening features wherein the single-pass yield of the n-butanol to the 2-ethylhexanal and/or the 2-ethylhexenal ranges from 1 percent to 80 percent, from 5 percent to 40 percent, or from 10 percent to 25 percent.

Embodiment C is a process for the preparation of 2-ethylhexanol comprising
(A) feeding n-butanol to a first reactor zone comprising a heterogeneous dehydrogenation catalyst to produce a butyraldehyde containing stream;
(B) feeding the butyraldehyde containing stream to a second reactor zone comprising a heterogeneous aldol condensation catalyst to produce a 2-ethylhexanal and/or 2-ethylhexenal containing stream; and
(C) hydrogenating the 2-ethylhexanal and/or 2-ethylhexenal containing stream to form a crude product comprising 2-ethylhexanal and/or 2-ethylhexanol;
wherein the process is conducted in the vapor phase The process of Embodiment C wherein the heterogeneous aldol condensation catalyst comprises $V_2O_5$ modified anatase.

The process of Embodiment C or Embodiment C with one or more of the intervening features wherein the heterogeneous aldol condensation catalyst comprises $V_2O_5$ modified anatase, wherein the amount of $V_2O_5$ ranges from 1 weight percent to 30 weight percent, from 2 weight percent to 20 weight percent, or from 5 weight percent to 15 weight percent based upon the total weight of the $V_2O_5$ modified anatase.

The process of Embodiment C or Embodiment C with one or more of the intervening features wherein the aldol condensation catalyst comprises $V_2O_5$ modified anatase, wherein the surface area of the $V_2O_5$ modified anatase ranges from 10 $m^2/g$ to 150 $m^2/g$ or from 20 $m^2/g$ to 100 $m^2/g$.

The process of Embodiment C or Embodiment C with one or more of the intervening features wherein the temperature ranges from 100° C. to 500° C. or from 100° C. to 350° C., and the pressure ranges from 0 psig to 250 psig or from 0 psig to 100 psig.

The process of Embodiment C or Embodiment C with one or more of the intervening features further comprising feeding a diluent gas selected from at least one of the group consisting of nitrogen, argon, oxygen, air, hydrogen, and helium to the first reactor zone, and wherein the molar ratio of the diluent gas to the n-butanol ranges from 0.1:1 to 20:1.

The process of Embodiment C or Embodiment C with one or more of the intervening features wherein the single-pass yield of the n-butanol to the 2-ethylhexanal and the 2-ethylhexanol ranges from 1 percent to 80 percent, from 5 percent to 60 percent, or from 10 percent to 40 percent.

EXAMPLES

Abbreviations—HBu=n-butyraldehyde; BuOH=n-butanol; EtOH=ethanol; HAc=acetaldehyde; HCr=crotonaldehyde; Dehydrated 2-EH products=2-ethylhexene isomers, 2-ethyhexane, 3-methyl-1,3-heptadiene; 2-EtHex-anol=2-EH=2-EH-ol=2-ethylhexanol; 2-EtHex-anal=2-EH-anal=2-EH-an-al=2-ethylhexanal; 2-Et-2-Hex-enal=2-EH-enal=2-EH-enal=2-ethylhexenal; tishchenko ester=butylbutyrate when butanol is fed or ethylaceate when ethanol is fed.

Calculations

Percent alcohol conversion=(moles of lower-molecular-weight alcohol fed−moles of lower-molecular-weight alcohol in product)/(moles of lower-molecular-weight alcohol fed)×100%

Moles of lower-molecular-weight aldehyde—When the lower-molecular-weight aldehyde is fed to the reactor, the moles of lower-molecular-weight aldehyde fed to the reactor are simply measured. When the lower-molecular-weight alcohol is fed to the reactor, the moles of lower-molecular-weight aldehyde "fed to the reactor" are calculated as the theoretical moles of lower-molecular-weight aldehyde formed by the dehydrogenation of the lower-molecular-weight alcohol. The theoretical moles of lower-molecular-weight aldehyde generated from the lower-molecular-weight alcohol is assumed to be the moles of lower-molecular-weight alcohol converted.

Percent conversion of lower-molecular-weight aldehyde=(moles of lower-molecular-weight aldehyde fed−moles of lower-molecular-weight aldehyde in product)/(moles of lower-molecular-weight aldehyde fed)×100%.

Selectivity to tishschenko ester=(0.5×moles of tishschenko ester in product)/(moles of lower-molecular-weight aldehyde or lower-molecular-weight alcohol converted)×100%.

Selectivity to higher-molecular-weight oxygenated products=(0.5×moles of higher-molecular-weight oxygenated products)/(moles of lower-molecular-weight aldehyde or lower-molecular-weight alcohol converted)×100%.

Selectivity to higher-molecular-weight dehydrated products=(0.5×moles of higher-molecular-weight deoxygenated products)/(moles of lower-molecular-weight aldehyde or lower-molecular-weight alcohol converted)×100%.

Yield of higher-molecular-weight oxygenated products=(percent conversion of lower-molecular-weight aldehyde or lower-molecular-weight alcohol)×(percent selectivity to higher-molecular-weight oxygenated products).

Percent mass balance=(mass of liquid product)/(mass of liquids fed to reactor)×100%.

Catalysts

Catalyst A—Catalyst A was prepared via modifications of the procedures reported in Reddy, B. M., et al., *J. Chem. Soc., Chem. Commun.* 1992, 997-998. To a 5 L flask was added 150.0 g of urea and 2 L of deionized water; the pH of this solution was about 5, as determined with pH paper. 49.67 g of zinc nitrate hexahydrate and 17.56 g of copper nitrate trihydrate were dissolved in the solution, then 20.0 g of gamma alumina (Alfa #44757) suspended in the resulting pale blue solution. The mixture was then heated to 98° C. for 3 hours, during which time the pH rose to about neutral. The mixture was then cooled to room temperature and the pale blue solid isolated on a glass frit and washed with deionized water (2 L) and air dried for 5 hours while pulling a vacuum. The light blue cake was then dried in a muffle furnace at 110° C. for 16 hours then sieved to 8×14 mesh and calcined at 450° C. in air in the muffle furnace for 20 hours to give dark gray particles.

Catalyst B—Catalyst B was a high surface area, unmodified anatase material, purchased from Alfa Aesar (#44429). The surface area was determined to be 158 $m^2/g$ by conventional BET measurement techniques.

Catalyst C—Catalyst C was a low surface area, unmodified anatase purchased from Evonik Degussa, Aerolyst 7708. The surface area was determined to be 47 $m^2/g$ by conventional BET measurement techniques.

Catalyst D—Catalyst D was prepared by impregnating Catalyst B with 27 wt % $V_2O_5$ via modifications of the procedures described in Reddy, B. M., et al., *Res. Chem. Intermed.* 1997, 23, 703-713. About 50 g of Catalyst B were impregnated twenty times with approximately 20 g of a 3.8% aqueous solution of vanadyl oxalate (prepared from a 2:1 molar mixture of oxalic acid and ammonium metavanadate). The rods were dried at 200° C. in air for two hours between each impregnation then calcined at 500° C. for two hours in a muffle furnace in air after the final impregnation.

Catalyst E—Catalyst E was prepared by soaking 20 g of Catalyst C in a 1M aqueous solution of vanadium trichloride for 2 hours. The rods were then filtered, washed with DI water and air dried for 1 hour. Further drying was achieved by placing the rods on a rotoevaporator and tumbling at 65 rpm while maintaining a bath temperature of 70° C. for 2 hours. The rods were then calcined at 500° C. in air for 2 hours. Elemental analysis showed that the rods contained 2.47 wt. % $V_2O_5$.

Catalyst F—Catalyst F was prepared by same procedure as Catalyst E. Catalyst F had a 2.9 wt % $V_2O_5$ loading.

Catalyst G—Catalyst G was a copper based catalyst, Pricat CU60/8T, purchased from Johnson Matthey.

Catalyst H—Catalyst H was a gold on silica catalyst, prepared by combining 37 g of a solution composed of 0.873 g $HAuCl_4 \times H_2O$ in 74 g of water with 21.9 g of silica (BASF) followed by stirring for ten minutes at pH=6.5. About 40 mL of 3% aqueous ammonia (pH=11) was then added and the mixture warmed to 60° C. for ten minutes. The catalyst powder was then filtered and air dried then reduced in a tube furnace at 140° C. for five hours with 5% hydrogen in nitrogen after a 1.5 hour temperature ramp.

Catalyst I—Catalyst I was prepared by crushing and mixing 7.0 g of Catalyst D with 14.0 g of Catalyst G. The powder was then compressed using a hydraulic press and the resulting disc crushed and sieved to 8×14 mesh.

Catalyst J—Octolyst 2006 available from Evonik Degussa. A commercial copper chromite catalyst crushed and sieved to 14-20 mesh.

Catalyst K—MgO extrudates available from Johnson Matthey crushed and sieved to 14-20 mesh.

Catalyst L—$Ca(OH)_2$ extrudates available from BASF Catalysts crushed and sieved to a 14-20 mesh.

Catalyst M—Aerolyst 7711, available from Evonik Degussa, a commercial version of anatase $TiO_2$.

Catalyst Regeneration Procedure—Catalysts A through G were charged to the reactor and used for various experimental runs. When catalysts A through G are listed as "regenerated" they have been through at least one cycle of catalytic use followed by flowing a stream of air at 400° C. over the catalyst for two hours.

Example 1

The reaction in this example was performed in a quartz reactor tube having indentations 5 inches up from the base of the tube. The region of the reactor with the indentations was situated near the base of the heated section of the furnace. The reactor was also fitted with a thermowell that extended from the top of the reactor to about an inch below the indentations. The reactor was first loaded with quartz chips to about nine inches in height above the indentations to allow the catalyst to be positioned in the center of the of the three-element furnace. The reactor was then loaded with a 1.46 g (10 mL) charge of Catalyst A. Quartz chips (about 7.5 inches) were added to the region above the catalyst charge. A three point thermocouple was then placed in the thermowell so that the middle thermocouple monitored the temperature of the catalyst bed. Heat to the reactor was provided by an Applied Test Systems series 3210 three-element electric furnace having a heated zone 19.5 inches in length. Liquid products were collected in a three-necked flask fitted with a glycol chilled (5° C.) jacket. The third neck of the flask was connected to a secondary receiver and dry ice trap apparatus which was connected to a glycol-cooled (5° C.) condenser. The base of each receiver flask was fitted with a stopcock to allow for draining of the liquid products.

Butanol was fed to the top of the reactor using an HPLC pump at a liquid feed rate of 0.2 mL/minute; nitrogen was used as diluent at a flow rate of 80 SCCM. The temperature of all three heated zones was set to 325° C. The liquid product was collected from both receivers after a three hour period. The contents of the receivers were combined and then analyzed by gas chromatography, the results from which are summarized in Table 1. These results correspond to 82.0% butanol conversion. Selectivities based on molar conversion of butanol: 9.2% selectivity to butylbutyrate and 80% selectivity to butyraldehyde. The single-pass yield of butanol to butyraldehyde was 66%. This example demonstrates that the copper-zinc catalyst is an acceptable catalyst for converting butanol into butyraldehyde.

Example 2

The experiment in this example was carried out as described in Example 1 except that the catalyst charge was 5.01 g (8.6 mL) of Catalyst B and the feed was butyraldehyde at 0.2 mL/min. Product samples were collected after two hours. The primary receiver product was homogenized with tetrahydrofuran (THF) due to a bilayer being present. Samples were analyzed by gas chromatography, the results from which are summarized in Table 1. These results correspond to 96% butyraldehyde conversion and the following molar selectivities: 0.0% selectivity to butylbutyrate, 19.2% selectivity to oxygenated 2-EH products and 2.7% selectivity to dehydrated 2-EH products. This example demonstrates that Catalyst B leads to high conversion of butyraldehyde with an 18.4% yield of oxygenated 2-EH products.

Comparative Example 1

The experiment in this example was carried out as described in Example 1 except that regenerated Catalyst B (5.01 g, 8.6 mL) was used as a catalyst; the reaction time was two hours. Product samples were analyzed by gas chromatography, the results from which are summarized in Table 1. These results correspond to 45.0% butanol conversion and 99.9% conversion of theoretical butyraldehyde. Selectivities based on molar conversion of butyraldehyde: 1.1% selectivity to butylbutyrate, 3.2% selectivity to oxygenated 2-EH products and 6.6% selectivity to dehydrated 2-EH products. These results show that Catalyst B affords more oxygenated 2-EH products and less dehydrated 2-EH products when butyraldehyde (see Example 2), rather than butanol, is used as the reactant.

Comparative Example 2

This example was carried out as described in Example 1 except that 5.02 g (5.4 mL) of regenerated Catalyst C was used as the catalyst. Product samples were collected after two hours and analyzed by gas chromatography, the results from which are summarized in Table 1. These results correspond to 13% butanol conversion and 99.9% conversion of theoretical butyraldehyde. Selectivities based on molar conversion of butyraldehyde: 0.1% selectivity to butylbutyrate, 2.4% selectivity to oxygenated 2-EH products and 2.5% selectivity to dehydrated 2-EH products. These results show that the low surface area anatase (Catalyst C) affords oxygenated 2-EH products in lower selectivity when butanol is used as the substrate than when butyraldehyde is used (see Example 3).

Example 3

The experiment in this example was carried out as described in Example 1 except that regenerated Catalyst C (5.02 g, 5.4 mL) was used as of the catalyst. The feed was butyraldehyde at 0.2 mL/min. Product samples were collected after two hours and analyzed by gas chromatography, the results from which are summarized in Table 1. These results correspond to 67% butyraldehyde conversion and the following molar selectivities: 0.3% selectivity to butylbutyrate, 90.0% selectivity to oxygenated 2-EH products and 0.2% selectivity to dehydrated 2-EH products. These results show that the lower surface area anatase catalyst (Catalyst C) affords higher selectivity to oxygenated 2-EH products when butyraldehyde is used as substrate than the higher surface area analogue (Catalyst B) employed in Example 2.

Comparative Example 3

The experiment in this example was carried out as described in Example 1 except that Catalyst D (5.0 g, 6 mL) was used as the catalyst; the reaction time was two hours. Product samples were analyzed by gas chromatography, the results from which are summarized in Table 1. These results correspond to 70.0% butanol conversion and 75.4% conversion of theoretical butyraldehyde. Selectivities based on molar conversion of butyraldehyde: 2.8% selectivity to butylbutyrate, 20.0% selectivity to oxygenated 2-EH products and 35.7% selectivity to dehydrated 2-EH products. These results show that Catalyst D is not as selective toward oxygenated 2-EH products when butanol, rather than butyraldehyde (see Example 4), is used as the substrate.

Example 4

The experiment in this example was carried out as described in Example 1 except that regenerated Catalyst D (5.0 g, 6 mL) was used as the catalyst. The feed was butyraldehyde at 0.2 mL/min. Product samples were collected after two hours and analyzed by gas chromatography, the results from which are summarized in Table 1. These results correspond to 42% butyraldehyde conversion and the following molar selectivities: 0.3% selectivity to butylbutyrate, 82.3% selectivity to oxygenated 2-EH products and 1.5% selectivity to dehydrated 2-EH products.

Comparative Example 4

The experiment in this example was carried out as described in Example 1 except that Catalyst E (5.02 g, 5.6 mL) was used as the catalyst. Product samples were collected after two hours and analyzed by gas chromatography, the results from which are summarized in Table 1. These results correspond to 46% butanol conversion and 99.2% conversion of theoretical butyraldehyde. Selectivities based on molar conversion of butyraldehyde: 10.0% selectivity to butylbutyrate, 10.5% selectivity to oxygenated 2-EH products and 37.5% selectivity to dehydrated 2-EH products. This example shows that when butanol, rather than butyraldehyde, is used as substrate the selectivity to oxygenated products is lower (see Example 5).

Example 5

The experiment in this example was carried out as described in Example 1 except that regenerated Catalyst E (5.02 g, 5.6 mL) was used. The feed was butyraldehyde at 0.2 ml/min. Product samples were collected after two hours and analyzed by gas chromatography, the results from which are summarized in Table 1. These results correspond to 70% butyraldehyde conversion and the following molar selectivities: 0.1% selectivity to butylbutyrate, 67.2% selectivity to oxygenated 2-EH products and 1.7% selectivity to dehydrated 2-EH products.

Example 6

The reaction in this example was carried out as described in Example 1 except that regenerated Catalyst E (5.02 g, 5.6 mL) was used. The feed was 0.2 mL/min. butyraldehyde, and the reactor was set to 200° C. instead of 325° C. Product samples were collected after two hours and analyzed by gas chromatography, the results from which are summarized in Table 1. These results correspond to 43% butyraldehyde conversion and the following molar selectivities: 0.0% selectivity to butylbutyrate, 99% selectivity to oxygenated 2-EH products and 0.3% selectivity to dehydrated 2-EH products. This example demonstrates that Catalyst E is more selective toward the desired oxygenated 2-EH products when operating at a lower reactor temperature (see Example 5). The butyraldehyde conversion was the same as that observed with Catalyst D in Example 4 even though the reactor temperature was 125° C. lower.

Comparative Example 5

The reaction was carried out as described in Example 1 except that the regenerated Catalyst E was used. The reactor temperature was then set to 300° C. instead of 325° C. Product samples were collected after two hours and analyzed by gas chromatography, the results from which are summarized in Table 1. These results correspond to 28% butanol conversion and 99.8% conversion of theoretical butyraldehyde. Selectivities based on molar conversion of butyraldehyde: 8.8% selectivity to butylbutyrate, 8.9% selectivity to oxygenated 2-EH products and 31.9% selectivity to dehydrated 2-EH products. This example shows that when butanol, rather than butyraldehyde (see Example 5), is used as substrate the selectivity to oxygenated products is considerably lower even when the reactor temperature is lowered by 25° C.

Example 7

The condensation reaction in this example was performed in the same quartz reactor tube described in Example 1 having indentations 5 inches up from the base of the tube. The region of the reactor with the indentations was situated near the base of the heated section of the furnace. The reactor was also fitted with a thermowell that extended from the top of the reactor to about an inch below the indentations. The reactor was first loaded with quartz chips to about two inches in height above the indentations to allow the catalyst to be positioned in the center of the bottom heated zone of the three-element furnace. The reactor was then loaded with a 5.01 g (8.6 mL) charge of Catalyst B. Sufficient quartz chips (about 13 inches) were added to the region above the catalyst charge to reach about an inch below the center of the top heated region of the three-element furnace. The reactor was then loaded with a 1.5 g (10.0 mL) charge of Catalyst A followed by about three inches of quartz chips. A three point thermocouple was then placed in the thermowell so that the temperature of each catalyst bed could be monitored via the top and bottom thermocouples. Heat to the reactor was provided by an Applied Test Systems series 3210 three-element electric furnace having a heated zone 19.5 inches in length. Liquid products were collected in a three-necked flask fitted with a glycol chilled (5° C.) jacket. The third neck of the flask was connected to a secondary receiver and dry ice trap apparatus which was connect to a glycol-cooled (5° C.) condenser. The base of each receiver flask was fitted with a stopcock to allow for draining of the liquid products.

Butanol was fed to the top of the reactor using an HPLC pump at a liquid feed rate of 0.2 mL/minute; nitrogen was used as diluent at a flow rate of 80 SCCM. The temperature of all three heated zones was set to 325° C. The liquid product was collected from both receivers after a two hour period; the primary receiver product was homogenized with tetrahydrofuran (THF) due to a bilayer being present. Samples were then analyzed by gas chromatography, the results from which are summarized in Table 1. These results correspond to 99% butanol conversion and 95.4% conversion of theoretical butyraldehyde. Selectivities based on molar conversion of butyraldehyde: 0.2% selectivity to butylbutyrate, 18.9% selectivity to oxygenated 2-EH related compounds and 6.9% selectivity to dehydrated 2-EH related compounds.

Example 8

The experiment in this example was carried out as described in Example 7 except that the first catalyst charged to the reactor was 5.02 g (6.8 mL) charge of Catalyst D; the reaction time was two hours. These results correspond to 94% butanol conversion and 57.3% conversion of theoretical butyraldehyde. Selectivities based on molar conversion of butyraldehyde: 5.6% selectivity to butylbutyrate, 54.8% selectivity to oxygenated 2-EH products and 7.0% selectivity to dehydrated 2-EH products. This example demonstrates that the Catalyst A forms only a slight amount of ester while generating butyraldehyde which undergoes aldol self-condensation over Catalyst D to form primarily 2-ethyl-2-hexenal along with other 2-EH related compounds.

Example 9

The experiment in this example was carried out as described in Example 7 except that 2.38 g (15 mL) of Catalyst A was charged to the top reactor zone and 6.01 g (5.5 mL) of Catalyst E was charged to the bottom zone. The top heated zone was set to 325° C., the middle to 250° C., and the bottom to 200° C. Product samples were collected after two hours and analyzed by gas chromatography, the results from which are summarized in Table 1. These results correspond to 88.4% butanol conversion and 47.5% conversion of theoretical butyraldehyde. Selectivities based on molar conversion of butyraldehyde: 12.3% selectivity to butylbutyrate, 33.7% selectivity to oxygenated 2-EH products and 0% selectivity to dehydrated 2-EH products. This example shows that essentially no dehydrated 2-EH products are formed when the low surface area anatase material (Catalyst E) is employed as the aldol catalyst.

Example 10

The experiment in this example was carried out as described in Example 7 except that 11.88 g (15 mL) of Catalyst G catalyst was charged to the top reactor zone and 14.64 g (15 mL) of a Catalyst F was charged to the bottom zone. The top heated zone was set to 300° C., the middle to 200° C. and the bottom to 125° C. The carrier gas in this example contained 6% oxygen in nitrogen. A product sample was collected after one hour and discarded then a final product sample collected after an additional five hours and analyzed by gas chromatography, the results from which are summarized in Table 1. These results correspond to 71.5% butanol conversion and 14.7% conversion of theoretical butyraldehyde. Selectivities based on molar conversion of butyraldehyde: 2.8% selectivity to butylbutyrate, 85.8% selectivity to oxygenated 2-EH products and 0% selectivity to dehydrated 2-EH products. This example shows that dehydrated $C_8$ products can be completely avoided with the dual catalyst configuration, and that the selectivity to the desired product is higher when the aldol condensation reaction is carried out at lower temperature.

Example 11

The experiment in this example was carried out as described in Example 7 except that 3.66 g (10 mL) of Catalyst H was charged to the top reactor zone and 9.41 g (10 mL) of Catalyst F was charged to the bottom zone. For the butanol condensation reaction the top heated zone of the two stage reactor was set to 325° C., the middle to 275° C. and the bottom to 200° C. The carrier gas in this example contained 6% oxygen in nitrogen. A product sample was collected after one hour and discarded then a final product sample collected after an additional five hours and analyzed by gas chromatography, the results from which are summarized in Table 1. These results correspond to 32.9% butanol conversion and 68.4% conversion of theoretical butyraldehyde. Selectivities based on molar conversion of butyraldehyde: 1.4% selectivity to butylbutyrate, 61.7% selectivity to oxygenated 2-EH related products and 0% selectivity to dehydrated 2-EH related products. This example shows that an exothermic oxidative dehydrogenation of butanol with a catalyst such as gold on silica followed by an aldol condensation also affords 2-ethylhexenal and essentially no dehydrated $C_8$ products (see Example 10).

Example 12

The experiment in this example was carried out as described in Example 1 except that the reactor temperature was set to 300° C. and 5.56 g (7 mL) of Catalyst I (Catalyst D dry mixed with Catalyst G) was used as the catalyst. Product samples were collected after two hours and analyzed by gas chromatography, the results from which are summarized in Table 1. These results correspond to 72.3% butanol conversion and 29.4% conversion of theoretical butyraldehyde. Selectivities based on molar conversion of butyraldehyde: 4.0% selectivity to butylbutyrate, 33.5% selectivity to oxygenated 2-EH products and 0% selectivity to dehydrated 2-EH products. This example demonstrates that dry mixing an alcohol dehydrogenation catalyst with an aldehyde condensation catalyst leads to a material that produces $C_8$ compounds with far less product dehydration than when Catalyst D is used as the sole catalyst (See Comparative Example 3).

TABLE 1

| Example | Mass Balance | Sample ID | Sample Mass (incl. THF) | HBu | THF | Butanol | Dehydrated 2-EH Products | 2-EtHex-anal | Butyl-butyrate | 2-Et-2-Hex-enal | 2-EtHex-anol |
|---|---|---|---|---|---|---|---|---|---|---|---|
| Ex 1 | 93% | 1° Rec. | 24.9 g | 66.2% | — | 20.6% | 0.09% | 0.4% | 8.6% | 0.2% | 0.06% |
|  |  | 2° Rec. | 2.36 g | 96.9% | — | 0.62 | 0.06% | 0.02% | 0.2% | 0.04% | — |
| Ex 2 | 90% | 1° Rec. | 54.89 g | 1.5% | 72.2% | 0.1% | 0.7% | 1.7% | 0.01% | 3.4% | 0.05% |
| CEx 1 | 79% | 1° Rec. | 23.03 g | 0.02% | 30.5% | 46.22 | 1.9% | 0.06% | 0.4% | 0.07% | 0.8% |
| CEx 2 | 93% | 1° Rec. | 18.45 g | 0.01% | — | 93.9% | 0.23% | 0.03% | 0.2% | 0.6% | 0.06% |
| Ex 3 | 94% | 1° Rec. | 32.17 g | 18.75% | 40.89% | 0.32% | 0.02% | 0.08% | 0.11% | 30.98% | — |
|  |  | 2° Rec. | 0.34 g | 95.62% | — | 1.51% | 0.16% | 0.03% | 0.01% | 0.48% | — |
| CEx 3 | 79% | 1° Rec. | 39.66 | 7.6% | 61.2% | 14.9% | 6.7% | 2.0% | 0.9% | 1.3% | 1.0% |
|  |  | 2° Rec. | 0.95 | 26.4% | — | 1.3% | 14.6% | 0.2% | 0.04% | 0.04% | — |
| Ex 4 | 95% | 1° Rec. | 30.11 g | 34.0% | 40.0% | 0.18% | 0.3% | 0.9% | 0.07% | 17.6% | 0.02% |
|  |  | 2° Rec. | 0.81 g | 83.8% | — | — | 0.3% | 0.04% | 0.01% | 0.4% | 0.01% |
| CEx 4 | 87% | 1° Rec. | 20.7 g | 0.04% | 18.2% | 50.4% | 11.7% | 0.8% | 3.9% | 0.9% | 1.9% |
|  |  | 2° Rec. | 0.38 g | 17.0% | — | 3.9% | 31.7% | 0.1% | 0.1% | 0.6% | — |
| Ex 5 | 92% | 1° Rec. | 39.32 g | 14.08% | 52.5% | 0.11%% | 0.45% | 1.28% | 0.05% | 18.33% | 0.01% |
| Ex 6 | 96% | 1° Rec. | 24.73 g | 41.19% | 25.45% | — | 0.07% | 0.09% | — | 28.22% | — |
|  |  | 2° Rec. | 0.64 g | 96.28% | — | 0.02% | 0.1% | 0.03% | — | 1.76% | — |
| CEx 5 | 90% | 1° Rec. | 17.48 g | 0.05% | — | 80.1% | 7.5% | — | 2.6% | 0.4% | 1.9% |
| Ex 7 | 84% | 1° Rec. | 55.75 g | 1.2% | 71.6% | 0.3% | 1.7% | 2.7% | 0.07% | 2.2% | 0.03% |
| Ex 8 | 86% | 1° Rec. | 30.32 g | 23.1% | 43.5% | 4.0% | 1.8% | 2.4% | 3.4% | 13.9% | 0.02% |
|  |  | 2° Rec. | 0.76 g | 93.4% | — | — | 2.4% | 0.08% | 0.08% | 0.21% | — |
| Ex 9 | 87% | 1° Rec. | 21.8 g | 37.59% | 32.34% | 8.02% | — | 0.57% | 8.96% | 10.17% | — |
|  |  | 2° Rec. | 0.59 g | 97.59% | — | 0.67% | — | 0.05% | 0.17% | 0.11% | — |
| Ex 10 | 100% | 1° Rec. | 54.88 g | 53.05% | 13.21% | 25.39% | — | 0.07% | 0.51% | 6.79% | — |
| EX 11 | 100% | 1° Rec. | 52.15 g | 9.52% | 5.59% | 63.01% | — | 1.2% | 0.56% | 9.95% | — |
| Ex 12 | 88% | 1° Rec. | 14.76 g | 50.01% | — | 35.81% | — | 2.98% | 2.19% | 5.04% | — |
|  |  | 2° Rec. | 2.41 g | 94.24% | — | 0.88% | — | 0.06% | 0.03% | 0.02% | — |

A series of control experiments were run to investigate the impact of Catalyst D on individual oxygenated 2-EH products. Comparative Examples 6-8 show that 2-ethylhexanol is unstable over the aldol condensation catalyst at typical reactor conditions whereas 2-ethylhexanal and 2-ethylhexenal are stable. These results reinforce the utility of the two stage catalyst invention which selectivity forms 2-EH aldehydes rather than 2-ethylhexanol.

Comparative Example 6

This example was carried out as described in Example 1 except that 5.01 g (5.5 mL) of regenerated Catalyst D was used as the catalyst and 0.2 mL/min of a commercially sourced 2-ethylhexanol (2-EH-ol, 99.7% purity) was used as the liquid feed. The reaction time was three hours. Product samples were analyzed by gas chromatography, the results from which are summarized in Table 2. This example demonstrates that an alcohol such as 2-ethylhexanol is unstable in the presence of Catalyst D. The 2-EH-ol conversion was 56% with 66% of the product being dehydrated to $C_8$ hydrocarbons and 36% being the saturated aldehyde, 2-EH-anal, which results from dehydrogenation of the alcohol moiety.

Comparative Example 7

The experiment in this example was carried out as described in Example 1 except that the catalyst charge was 5.01 g (5.5 mL) of regenerated Catalyst D and 0.2 mL/min of a commercially sourced 2-ethylhexenal (2-EH-enal, 95.5% purity) was used as the liquid feed. The reaction time was three hours. Product samples were analyzed by gas chromatography, the results from which are summarized in Table 2. This example demonstrates that an unsaturated aldehyde such as 2-ethylhexenal is stable in the presence of Catalyst D.

Comparative Example 8

The experiment in this example was carried out as described in Example 1 except that the catalyst charge was 5.01 g (5.5 mL) of regenerated Catalyst D and 0.2 mL/min of a commercially sourced 2-ethylhexanal (2-EH-anal, 99.8% purity) was used as the liquid feed. The reaction time was three hours. Product samples were analyzed by gas chromatography, the results from which are summarized in Table 2. This example demonstrates that a saturated aldehyde such as 2-ethylhexanal is stable in the presence of Catalyst D. The 2-EH-enal conversion was less than one percent and dehydrated $C_8$ compounds were not detected.

TABLE 2

| Example | Liquid Feed | Mass Balance | Sample Mass (incl. THF) | THF | Dehydrated 2-EH Products | 2-EtHex-anal | 2-Et-2-Hex-enal | 2-EtHex-anol |
|---|---|---|---|---|---|---|---|---|
| Comp. Ex. 6 | 2-EH-ol | 90% | 43.57 | 27.16% | 23.6% | 14.47% | 0.04% | 31.19% |
| Comp. Ex. 7 | 2-EH-enal | 99% | 36.64 | 17.73% | — | 1.52% | 71.54% | — |
| Comp. Ex. 8 | 2-EH-anal | 98% | 37.95 | 24.7% | — | 70.29% | 0.9 | — |

Example 13

The reactor for this example was comprised of a feed system, preheater, reactor, condenser, and product tank. The feed system was a vertically mounted glass feed tank holding approximately 50 mL of feed alcohol. The feed was pumped through an Eldex brand HPLC pump with stainless steel wetted parts and a maximum feed rate of 20 mL/min. Gas feed was delivered through a Brooks mass flow controller with a maximum feed rate of 1 SLPM. The feed rate was controlled by an electronic controller external to the flow controller. The liquid feed and gas feeds passed through ¼" O.D. stainless steel tubing before mixing at a "tee" prior to entering the preheater. The preheater was constructed of 18" of 0.5" O.D. stainless steel tubing packed with inert fused alumina pellets. The preheater was wrapped in electrical heat tape and insulated. The heat tape was controlled by an external thermostat. A K-type thermocouple was mounted top down into the preheater to allow for internal measurement. Typically the preheater internal temperature was held at 120° C.

The reactor was constructed of a 24"×0.5" O.D. length of tubing mounted vertically in a clam shell type single zone furnace. The furnace was controlled by an external heating source. Two K-type thermocouples were mounted into the furnace from the top and bottom. The bottom thermocouple extended 0.5" to 1" into the bottom of the catalyst bed. The furnace heater was adjusted to maintain a constant temperature at the bottom of the catalyst bed. The effluent of the preheater entered the reactor at the top and traveled down through several inches of inert fused alumina before contacting the catalyst bed.

The reactor effluent exited through the bottom of the reactor and entered a shell in tube type condenser. The cooling medium was chilled glycol and a K-type thermocouple was mounted in the tube side to monitor effluent temperature. Effluent leaving the condenser was typically 18 to 19° C.

The condenser effluent entered an armored sight glass that served as a product tank. Uncondensed gases exited the top of a tank through a vent line. A back pressure regulator was mounted on the vent line and served to control reaction pressure in the entire system. The vent gases exited the back pressure regulator and passed through a dry ice trap where any other condensables were removed. The liquid samples from the product tank and dry ice trap were combined and weighed hourly. They were analyzed by GC. The vent gases were periodically collected, the flow measured, and analyzed by GC.

The continuous reactor described above was charged with 12 mL of Catalyst J. The reactor was brought to 350° C. at atmospheric pressure. An $N_2$ stream at 600 SCCM was introduced. Ethanol was fed into the reactor at 0.15 mL/min. Liquid and gas samples were taken periodically over a 7 hour period and analyzed by gas chromatogram. The effluent was found to contain 68.2% acetaldehyde, 21.2% ethanol, 3.3% crotonaldehyde, 2.8% normal butyraldehyde, 1.9% water, 0.9% normal butanol, and the balance components with wt %<0.5%. This corresponds to 79% conversion of ethanol. Selectivities based on molar conversion of ethanol: 1.1% selectivity to butanol, and 10.8% selectivity to $O_4$ oxygenated compounds, crotonaldehyde, butyraldehyde, and butanol.

Example 14

Example 13 was repeated with an $N_2$ stream of 250 SCCM. The effluent was found to contain 60.4% acetaldehyde, 20.6% ethanol, 9.1% normal butyraldehyde, 1.9% $CO_2$, 1.7% normal butanol, 1.3% crotonaldehyde, 1.2% ethyl acetate and the balance components with weight %<0.8%. This corresponds to 85% conversion of ethanol. Selectivities based on molar conversion of ethanol: 2.3% selectivity to butanol, and 17.3% selectivity to $C_4$ oxygenated compounds, crotonaldehyde, butyraldehyde, and butanol.

Comparative Example 9

Example 13 was repeated except the continuous reactor was charged with 12 mL of Catalyst K. Liquid and gas samples were taken periodically over a 7 hour period and analyzed by gas chromatogram. The effluent was found to contain 95.6% ethanol, 1.2% acetaldehyde, 1.8% water, 1.0% normal butanol, and the balance trace amounts of crotonaldehyde and ethyl acetate. This corresponds to 5.5% conversion of ethanol.

Example 15

Example 13 was repeated except the continuous reactor was charged with a bottom catalyst bed of 8 mL of Catalyst L. A top catalyst bed of 12 mL of Catalyst J was laid on top of Catalyst L. Liquid and gas samples were taken periodically over a 6 hour period and analyzed by gas chromatogram. The effluent was found to contain 71.0% acetaldehyde, 12.8% ethanol, 1.3% crotonaldehyde, 7.5% normal butyraldehyde, 1.5% $CO_2$, 1.2% propylene, 0.5% normal butanol, and the balance components with wt %<0.5%. This corresponds to 87.4% conversion of ethanol and 16% conversion of theoretical acetaldehyde. Selectivities based on molar conversion of acetaldehyde: 3.6% selectivity to butanol, 67.0% selectivity to $O_4$ oxygenated compounds, and 2.4% selectivity to $C_8$ oxygenated compounds, 2-ethylhexanal, 2-ethylhexenal, and 2EH.

Example 16

Example 13 was repeated except the continuous reactor was charged with a bottom catalyst bed of 8 mL of Catalyst K and a top catalyst bed of 12 mL of Catalyst J which was laid on top of Catalyst K. The reactor was brought to 350° C. under ambient pressure. A $N_2$ stream of 600 SCCM was introduced and ethanol fed at 0.15 mL/min. Liquid and gas samples were taken periodically over a 7 hour period and analyzed by gas chromatogram. The effluent was found to contain 75.0% acetaldehyde, 10.5% ethanol, 4.5% normal butyraldehyde, 2.8% $H_2O$, 1.8% crotonaldehyde, 1.5% 2-ethyl-crotonaldehyde, 0.8% ethyl acetate, 0.7% normal butanol, and the balance components with wt %<0.6%. This corresponds to 85% conversion of ethanol and 15% conversion of theoretical acetaldehyde. Selectivities based on molar conversion of acetaldehyde: 5.3% selectivity to butanol, 58.2% selectivity to $C_4$ oxygenated compounds, and 19.8% selectivity to $C_8$ oxygenated compounds, 2-ethylhexanal, 2-ethylhexenal, and 2EH.

Example 17

Example 16 was repeated except the reactor was brought to 350° C. under 125 psig pressure. A $N_2$ stream of 400 SCCM was introduced and ethanol fed at 0.15 mL/min. Liquid and gas samples were taken periodically over a 5 hour period and analyzed by gas chromatogram. The effluent was found to contain 56.2% acetaldehyde, 21% ethanol, 11% normal butyraldehyde, 3.6% $H_2O$, 1.6% normal butanol, 1.5% crotonaldehyde, 0.5% 2-ethyl-crotonaldehyde, 0.9% ethyl butyrate and the balance components with wt %<0.6%. This corresponds to 81% conversion of ethanol and 34% conversion of theoretical acetaldehyde. Selectivities based on molar conversion of acetaldehyde: 8.2% selectivity to butanol, 73% selectivity to $C_4$ oxygenated compounds, crotonaldehyde, butyraldehyde, and butanol, and 5.0% selectivity to $C_8$ oxygenated compounds, 2-ethylhexanal, 2-ethylhexenal, and 2-ethylhexanol.

Example 18

Example 13 was repeated except the continuous reactor was charged with a bottom catalyst bed of 15 mL of Catalyst M and a top catalyst bed of 10 mL of Catalyst J which was laid on top of Catalyst M. The reactor was brought to 350° C. under ambient pressure. A $N_2$ stream of 600 SCCM was introduced and ethanol fed at 0.15 mL/min. Liquid and gas samples were taken periodically over a 6 hour period and analyzed by gas chromatogram. The effluent was found to contain 40.5% acetaldehyde, 34.2% ethanol, 10.9% $H_2O$, 4.4% normal butyraldehyde, 3.5% crotonaldehyde, 2.1% acetone, 0.9% ethyl acetate, and the balance components with wt %<0.5%. This corresponds to 66% conversion of ethanol and 37% conversion of theoretical acetaldehyde. Selectivities based on molar conversion of acetaldehyde: 53% selectivity to $C_4$ oxygenated compounds, crotonaldehyde, butyraldehyde, and butanol, and 6% selectivity to $C_8$ oxygenated compounds, 2-ethylhexanal, 2-ethylhexenal, and 2-ethylhexanol.

Example 19

Example 13 was repeated except the continuous reactor was charged with a bottom catalyst bed of 35 mL of Catalyst K and a top catalyst bed of 18 mL of Catalyst J which was laid on top of Catalyst K. The reactor was brought to 350° C. under ambient pressure. A $N_2$ stream of 750 SCCM was introduced and normal butanol was fed at 0.25 mL/min. Liquid and gas samples were taken periodically over a 6 hour period and analyzed by gas chromatogram. The effluent was found to contain 57.3% butanol, 31.7% normal butyraldehyde, 4.1% 2-ethylhexenal, 1.9% butyl butyrate, 1.8% H2O, 0.8% 2-ethylhexanal, 0.5% 2-ethylhexanol and the balance components with wt %<0.4%. This corresponds to 44% conversion of butanol and 30% conversion of theoretical normal butyraldehyde. Selectivities based on molar conversion of butyraldehyde: 5.3% selectivity to 2-ethylhexanol and 58.1% selectivity to all $C_8$ oxygenated compounds.

Example 20

Example 13 was repeated except the continuous reactor was charged with a bottom catalyst bed of 15 mL of Catalyst M and a top catalyst bed of 10 mL of Catalyst J which was laid on top of Catalyst M. The catalyst was the same as that used in Example 18: the reactor was purged with inert gas between Example 18 and Example 20. Normal butanol was fed at 0.25 mL/min. Liquid and gas samples were taken periodically over a 7 hour period and analyzed by gas chromatogram. The effluent was found to contain 59.4% butanol, 24.4% normal butyraldehyde, 5.0% 2-ethylhexenal, 6.8% H2O, 1.0% 2-ethylhexanal, 0.8% butyl butyrate, 0.8% 2-ethylhexanol and the balance components with wt %<0.4%. This corresponds to 44% conversion of butanol and 46% conversion of theoretical normal butyraldehyde. Selectivities based on molar conversion of butyraldehyde: 7.6% selectivity to 2-ethylhexanol and 62.3% selectivity to $C_8$ oxygenated compounds.

Example 21

Example 20 was repeated except the continuous reactor was brought to 350° C. under ambient pressure. Normal butanol was fed at 0.15 mL/min. Liquid and gas samples were taken periodically over a 7 hour period and analyzed by gas chromatogram. The effluent was found to contain 76.4% butanol, 14.1% normal butyraldehyde, 3.6% 2-ethylhexenal, 2.1% H2O, 1.0% 2-ethylhexanal, 0.7% butyl butyrate, 0.9% 2-ethylhexanol and the balance components with wt %<0.4%. This corresponds to 44% conversion of butanol and 46% conversion of theoretical normal butyraldehyde. Selectivities based on molar conversion of butyraldehyde: 11.8% selectivity to 2-ethylhexanol and 73.0% selectivity to $C_8$ oxygenated compounds.

The invention has been described in detail with particular reference to preferred embodiments thereof, but it will be understood that variations and modifications can be effected within the spirit and scope of the invention.

We claim:

1. A process for the preparation of a higher-molecular-weight alcohol comprising
    (A) feeding a lower-molecular-weight alcohol to a first reactor zone comprising a heterogeneous dehydrogenation catalyst to produce a lower-molecular-weight aldehyde containing stream;
    (B) feeding said lower-molecular-weight aldehyde containing stream to a second reactor zone comprising a heterogeneous aldol condensation catalyst to produce a higher-molecular-weight aldehyde containing stream; and
    (C) feeding said higher-molecular-weight aldehyde containing stream and hydrogen to a third reactor zone comprising a heterogeneous hydrogenation catalyst to produce an effluent comprising a higher-molecular-weight alcohol;
    wherein said process is conducted in the vapor phase.

2. The process according to claim 1, wherein said heterogeneous aldol condensation catalyst comprises $V_2O_5$ modified anatase.

3. The process according to claim 1, wherein said lower-molecular-weight alcohol is selected from the group consisting of methanol, ethanol, n-propanol, n-butanol, and i-butanol.

4. The process according to claim 1, wherein the temperature ranges from 100° C. to 500° C., the pressure ranges from 0 psig to 250 psig; and further comprising feeding a diluent gas selected from at least one of the group consisting of nitrogen, argon, oxygen, air, hydrogen, and helium to said first reactor zone.

5. The process according to claim 1, wherein the single-pass yield of lower-molecular-weight alcohol to higher-molecular-weight alcohol ranges from 5 percent to 60 percent.

6. A process for the preparation of 2-EH compounds comprising
    (A) feeding n-butanol to a first reactor zone comprising a heterogeneous dehydrogenation catalyst and a heterogeneous aldol condensation catalyst; and
    (B) producing a reactor effluent comprising at least one compound selected from the group consisting of 2-ethylhexanal (2-EH-anal) and 2-ethylhexenal (2-EH-enal);
    wherein said process is conducted in the vapor phase.

7. The process according to claim 6, wherein said heterogeneous dehydrogenation catalyst and said heterogeneous aldol condensation catalyst are commingled in a catalyst bed.

8. The process according to claim 6, wherein said heterogeneous dehydrogenation catalyst is in a first catalyst bed and said heterogeneous aldol condensation catalyst is in a second catalyst bed.

9. The process according to claim 6, further comprising
    (C) feeding said reactor effluent to a second reactor zone comprising a heterogeneous hydrogenation catalyst to produce a crude product comprising of 2-ethylhexanal and/or 2-ethylhexanol.

10. The process according to claim 6, wherein said heterogeneous aldol condensation catalyst comprises $V_2O_5$ modified anatase.

11. The process according to claim 10, wherein said heterogeneous aldol condensation catalyst comprises $V_2O_5$ modified anatase, wherein the amount of $V_2O_5$ ranges from 1 weight percent to 30 weight percent based upon the total weight of said $V_2O_5$ modified anatase.

12. The process according to claim 6, wherein the temperature ranges from 100° C. to 500° C.

13. The process according to claim 6, wherein the temperature ranges from 100° C. to 350° C.

14. The process according to claim 6, wherein the pressure ranges from 0 psig to 250 psig.

15. The process according to claim 6, wherein the pressure ranges from 0 psig to 100 psig.

16. The process according to claim 6, further comprising feeding a diluent gas selected from at least one of the group consisting of nitrogen, argon, oxygen, air, hydrogen, and helium to said first reactor zone.

17. The process according to claim 6, wherein the single-pass yield of said n-butanol to said 2-ethylhexanal and/or said 2-ethylhexenal ranges from 10 percent to 60 percent.

18. The process according to claim 9, wherein the single-pass yield of said n-butanol to said 2-ethylhexanal and/or said 2-ethylhexanol ranges from 5 percent to 40 percent.

19. A process for the preparation of 2-ethylhexanol comprising
    (A) feeding n-butanol to a first reactor zone comprising a heterogeneous dehydrogenation catalyst to produce a butyraldehyde containing stream;
    (B) feeding said butyraldehyde containing stream to a second reactor zone comprising a heterogeneous aldol condensation catalyst to produce a 2-ethylhexanal and/or 2-ethylhexenal containing stream; and
    (C) hydrogenating said 2-ethylhexanal and/or 2-ethylhexenal containing stream to form a crude product comprising 2-ethylhexanal and/or 2-ethylhexanol
    wherein said process is conducted in the vapor phase.

20. The process according to claim 19, wherein said heterogeneous aldol condensation catalyst comprises $V_2O_5$ modified anatase.

21. The process according to claim 19, wherein said heterogeneous aldol condensation catalyst comprises $V_2O_5$ modified anatase, wherein the amount of $V_2O_5$ ranges from 1 weight percent to 30 weight percent based upon the total weight of said $V_2O_5$ modified anatase.

22. The process according to claim 19, wherein said aldol condensation catalyst comprises $V_2O_5$ modified anatase, wherein the surface area of said $V_2O_5$ modified anatase ranges from 10 $m^2/g$ to 150 $m^2/g$.

23. The process according to claim 19, wherein the temperature ranges from 100° C. to 500° C. and the pressure ranges from 0 psig to 250 psig.

24. The process according to claim 19, wherein the temperature ranges from 100° C. to 350° C. and the pressure ranges from 0 psig to 100 psig.

25. The process according to claim 19, further comprising feeding a diluent gas selected from at least one of the group consisting of nitrogen, argon, oxygen, air, hydrogen, and helium to said first reactor zone, and wherein the molar ratio of said diluent gas to said n-butanol ranges from 0.1:1 to 20:1.

26. The process according to claim 19, wherein the single-pass yield of said n-butanol to said 2-ethylhexanal and said 2-ethylhexanol ranges from 5 percent to 60 percent.

27. A process for the preparation of 2-ethylhexanol comprising
- (A) feeding ethanol to a first reactor zone comprising a first heterogeneous dehydrogenation catalyst to produce an acetaldehyde containing stream;
- (B) feeding said acetaldehyde containing stream to a second reactor zone comprising a first heterogeneous aldol condensation catalyst to produce a crotonaldehyde containing stream;
- (C) feeding said crotonaldehyde containing stream to a third reactor zone comprising a first hydrogenation catalyst to produce a n-butanol containing stream;
- (D) feeding said n-butanol containing stream to a fourth reactor zone comprising a second heterogeneous dehydrogenation catalyst to produce a butyraldehyde containing stream;
- (E) feeding said butyraldehyde containing stream to a fifth reactor zone comprising a second heterogeneous aldol condensation catalyst to produce a 2-ethylhexanal and/or 2-ethylhexenal containing stream; and
- (F) feeding said 2-ethylhexanal and/or 2-ethylhexenal containing stream to a sixth reactor zone comprising a second hydrogenation catalyst to produce a crude product comprising 2-ethylhexanol wherein said process is conducted in the vapor phase.

* * * * *